(12) United States Patent
Donahue

(10) Patent No.: US 7,732,204 B2
(45) Date of Patent: Jun. 8, 2010

(54) CELL CULTURE METHOD AND APPARATUS FOR MECHANICALLY STIMULATING CELLS

(75) Inventor: Seth W. Donahue, Houghton, MI (US)

(73) Assignee: Michigan Technological University, Houghton, MI (US)

(*) Notice: Subject to any disclaimer, the term of this patent is extended or adjusted under 35 U.S.C. 154(b) by 1437 days.

(21) Appl. No.: 11/108,403

(22) Filed: Apr. 18, 2005

(65) Prior Publication Data
US 2006/0234372 A1    Oct. 19, 2006

(51) Int. Cl.
*C12M 3/00* (2006.01)
*C12N 5/00* (2006.01)

(52) U.S. Cl. .......... 435/395; 435/286.5; 435/293.1; 435/299.1; 623/915

(58) Field of Classification Search .............. 435/286.1, 435/286.5, 293.1, 299.1, 395–402; 623/915, 623/916, 919
See application file for complete search history.

(56) References Cited

U.S. PATENT DOCUMENTS

| | | | | |
|---|---|---|---|---|
| 6,114,164 | A | * | 9/2000 | Dennis et al. ............ 435/286.1 |
| 6,358,532 | B2 | * | 3/2002 | Starling et al. ............... 424/489 |
| 6,607,910 | B1 | | 8/2003 | Dimitrijevich et al. |
| 2002/0042701 | A1 | * | 4/2002 | Dancu et al. .................... 703/9 |

OTHER PUBLICATIONS

Alford et al. "Oscillating fluid flow regulates gap junction communication in osteocytic ML)-Y4 cells by an ERK1/2 MAP kinase-dependent mechanism." Bone, vol. 33 (2003), pp. 64-70.*
Batra et al. "Effects of short-term recovery periods on fluid-induced signalling in osteoblastic cells." Journal of Biomechanics, vol. 38, Is. 9, pp. 1909-1917, Available online Oct. 1, 2004.*
Batra et al. "Effect of Short Term Recovery Periods on Fluid Shear Induced Calcium Oscillations in Osteoblastic Cells." Medicine & Science in Sports & Exercise: vol. 35, No. 5 (May 2003), p. S4.*
Donahue et al. "Osteoblastic cells have refractory periods for fluid-flow-induced intracellular calcium oscillations for short bouts of flow and display multiple low-magnitude oscillations during long-term flow." Journal of Biomechanics, vol. 36 (2003), pp. 35-43.*

(Continued)

*Primary Examiner*—William H Beisner
(74) *Attorney, Agent, or Firm*—Michael Best & Friedrich LLP

(57) ABSTRACT

A cell culture assembly and a method for culturing cells that provide mechanical stimulation to cells. The cell culture assembly can include a flow chamber positioned in a fluid path and a support comprising cells positioned within the flow chamber to expose the cells to the fluid path. The cell culture assembly can further include a means for producing a steady flow of fluid in the fluid path, and a means for producing an oscillatory flow of fluid in the fluid path simultaneously with producing the steady flow of fluid in the fluid path to mechanically stimulate the cells. The method can include transporting fluid in the fluid path at a substantially steady flow rate, and transporting fluid in the fluid path at a substantially oscillatory flow rate simultaneously with transporting fluid in the fluid path at a substantially steady flow rate.

8 Claims, 3 Drawing Sheets

OTHER PUBLICATIONS

Klein-Nulend et al., Pulsating Fluid Flow Stimulates Prostaglandin Release and Inducible Prostaglandin G/H Synthase mRNA Expression in Primary Mouse Bone Cells, Journal Of Bone and Mineral Research, vol. 12, No. 1, pp. 45-51, 1997.

Klein-Nulend et al., Recent Advances in Human Biology, Response of Isolated Osteocytes to Mechanical Loading In Vitro, World Scientific, vol. 2, pp. 37-49, 1994.

Reilly et al., Fluid Flow Induced $PGE_2$ Release by Bone Cells is Reduced by Glycocalyx Degradation Whereas Calcium Signals Are Not, Biorheology, vol. 40, pp. 591-603, 2003.

Smalt et al., Induction of NO and Prostaglandin $E_2$ in Osteoblasts by Wall-Sheer Stress but Not Mechanical Strain, The American Journal of Physiology: Endocrinology and Metabolism, vol. 273:36, pp. E751-E758, 1997.

Reich et al., Effect of Flow on Prostaglandin $E_2$ and Inositol Trisphosphate Levels in Osteoblasts, The American Journal of Physiology: Cell Physiology, vol. 261:30, pp. C428-C432, 1991.

Bakker et al., The Production of Nitric Oxide and Prostaglandin $E_2$ by Primary Bone Cells is Sheer Stress Dependent, Journal of Biomechanics, vol. 34, pp. 671-677, 2001.

Nauman et al., Osteoblasts Respond to Pulsatile Fluid Flow with Short-Term Increases in $PGE_2$ but No Change in Mineralization, Journal of Applied Physiology, vol. 90, pp. 1849-1854, 2001.

Owan et al., Mechanotransduction in Bone: Osteoblasts are More Responsive to Fluid Forces Than Mechanical Strain, American Journal of Physiology: Cell Physiology, vol. 273:42, pp. C810-C815, 1997.

Bakker et al., Shear Stress Inhibits While Disuse Promotes Osteocyte Apoptosis, Biochemical and Biophysical Research Communications, vol. 320, pp. 1163-1168, Jun. 25, 2004.

Cheng et al., Expression of Functional Gap Junctions and Regulation by Fluid Flow in Osteocyte-Like MLO-Y4 Cells, Journal of Bone and Mineral Research, vol. 16, No. 2, pp. 249-259, 2001.

Allen et al., Serum Modulates the Intracellular Calcium Response of Primary Cultured Bone Cells to Shear Flow, Journal of Biomechanics, vol. 33, pp. 1585-1591, 2000.

Ryder et al., Parathyroid Hormone Modulates the Response of Osteoblast-Like Cells to Mechanical Stimulation, Calcified Tissue International, vol. 67, pp. 241-246, 2000.

You et al., Osteopontin Gene Regulation by Oscillatory Fluid Flow via Intracellular Calcium Mobilization and Activation of Mitogen-activated Protein Kinase in MC3T3-E1 Osteoblasts, Journal of Biological Chemistry, vol. 276, No. 16, pp. 13365-13371, Jan. 26, 2001.

Pavalko et al., Fluid Shear-Induced Mechanical Signaling in MC3T3-E1 Ostoblasts Requires Cytoskeleton-Integrin Interactions, American Journal of Physiology: Cell Physiology, vol. 275, pp. C1591-C1601, 1998.

Saunders et al., Cell Physiology, Gap Junctions and Fluid Flow Response in MC3T3-E1 Cells, American Journal of Physiology: Cell Physiology, vol. 281, pp. C1917-C1925, 2001.

Ryder et al., Parathyroid Hormone Enhances Fluid Shear-Induced $[Ca^{2+}]_i$ Signaling in Osteoblastic Cells Through Activation of Mechanosensitive and Voltage-Sensitive $Ca^{2+}$ Channels, Journal of Bone and Mineral Research, vol. 16, No. 2, pp. 240-248, 2001.

Jacobs et al., Differential Effect of Steady Versus Oscillating Flow on Bone Cells, Journal of Biomechanics, vol. 31, pp. 969-976, 1998.

Hung et al., Real-Time Calcium Response of Cultured Bone Cells to Fluid Flow, Clinical Orthopaedics and Related Research, No. 313, pp. 256-269, Apr. 1995.

Elfervig et al., IL-1β Sensitizes Intervertebral Disc Annulus Cells to Fluid-Induced Shear Stress, Journal of Cellular Biochemistry, vol. 82, pp. 290-298, 2001.

Barbee et al., Subcellular Distribution on Shear Stress at the Surface of Flow-Aligned and Nonaligned endothelial Monolayers, American Journal of Physiology: Heart and Circulatory Physiology, vol. 268:37, pp. H1765-H1772, 1995.

Abbott, Biology's New Dimension, Nature, vol. 424, pp. 870-872, Aug. 21, 2003.

Goodbye, Flat Biology?, Nature, vol. 424, No. 6951, pp. 861-862, Aug. 21, 2003.

Shu et al., Hydroxyapatite Accelerates Differentiation and Suppresses Growth of MC3T3-E1 Osteoblasts, Journal of Biomedical Materials Research, vol. 67A, pp. 1196-1204, 2003.

Sikavitsas et al., Mineralized Matrix Deposition by Marrow Stromal Osteoblasts in 3D Perfusion Culture Increases with Increasing Fluid Shear Forces, Proceedings of the National Academy of Sciences, vol. 100, No. 25, pp. 14683-14688, Dec. 9, 2003.

Hillsley et al., Bone Tissue Engineering: The Role of Interstitial Fluid Flow, Biotechnology and Bioengineering Review, vol. 43, No. 7, pp. 573-581, 1994, Mar. 25, 1994.

Goldstein et al., Effect of Convection on Ostoblastic Cell Growth and Function in Biodegradable Polymer Foam Scaffolds, Biomaterials, vol. 22, pp. 1279-1288, 2001.

Cartmell et al., Effects of Medium Perfusion Rate on Cell-Seeded Three-Dimensional Bone Constructs in Vitro, Tissue Engineering, vol. 9, No. 6, pp. 1197-1203, 2003.

Bancroft et al., Design of a Flow Perfusion Bioreactor System for Bone Tissue-Engineering Applications, Tissue Engineering, vol. 9, No. 3, pp. 549-554, 2003.

Cheng et al., Expression of Functional Gap Junctions and Regulation by Fluid Flow in Osteocyte-Like MLO-Y4 Cells, Journal of Bone and Mineral Research, vol. 16, No. 2, pp. 249-259, 2001.

Nauman et al., Quantitative Assessment of Steady and Pulsatile Flow Fields in a Parallel Plate Flow Chamber, Annals of Biomedical Engineering, vol. 27, pp. 194-199, 1999.

Marsano et al., Paper No. 0273, Oscillating Fluid Flow Through 3-D Scaffolds Enhances Cell Seeding Efficiency and Uniformity, presented at the $49^{th}$ Annual Mtg. of the Orthopaedic Research Society, New Orleans, Louisiana, Feb. 2-5, 2003, 1 page.

Yang et al., Induction of Human Osteoprogenitor Chemotaxis, Proliferation, Differentiation, and Bone Formation by Ostoblast Stimulating Factor-1/Pleiotrophin: Osteoconductive Biomimetic Scaffolds for Tissue Engineering, Journal of Bone and Mineral Research, vol. 18, No. 1, pp. 47-57, 2003.

Sikavitsas et al., Formation of Three-Dimensional Cell/Polymer Constructs for Bone Tissue Engineering in a Spinner Flask and a Rotating Wall Vessel Bioreactor, Wiley InterScience, pp. 136-147, Jul. 3, 2002.

Mendes et al., Bone Tissue-Engineered Implants Using Human Bone Marrow Stromal Cells: Effect of Culture Conditions and Donor Age, Tissue Engineering, vol. 8, No. 6, pp. 911-920, 2002.

Masuda et al., Post-Natal Endothelial Progenitor Cells for Neovascularization in Tissue Regeneration, Cardiovascular Research, vol. 58, pp. 390-398, 2003.

Ehara et al., Effects of α-TCP and TetCP on MC3T3-E1 Proliferation, Differentiation and Mineralization, Biomaterials, vol. 24, pp. 831-836, 2003.

Cerroni et al., Growth of Osteoblast-Like Cells on Porous Hydroxyapatite Ceramics: an In Vitro Study, Biomolecular Engineering, vol. 19, pp. 119-124, 2002.

Athanasiou et al., Fundamentals of Biomechanics in Tissue Engineering of Bone, Tissue Engineering, vol. 6, No. 4, pp. 361-381, 2000.

Botchwey et al., Human Osteoblast-Like Cells in Three-Dimensional Culture with Fluid Flow, Biorheology, vol. 40, pp. 299-306, 2003.

Holy et al., Engineering Three-Dimensional Bone Tissue in vitro Using Biodegradable Scaffolds: Investigating Initial Cell-Seeding Density and Culture Period, Journal of Biomedical Materials Research, vol. 51, pp. 376-382, 2000.

Meinel et al., Bone Tissue Engineering Using Human Mesenchymal Stem Cells: Effects of Scaffold Material and Medium Flow, Annals of Biomedical Engineering, vol. 32, No. 1, pp. 112-122, 2004.

Ishaug et al., Bone Formation by Three-Dimensional Stromal Osteoblast Culture in Biodegradable Polymer Scaffolds, Journal of Biomedical Materials Research, vol. 36, pp. 17-28, 1997.

Wang et al., Application of Perfusion Culture System Improves in Vitro and in Vivo Osteogenesis of Bone Marrow-Derived Osteoblastic Cells in Porous Ceramic Materials, Tissue Engineering, vol. 9, No. 6, pp. 1205-1214, 2003.

Langstaff et al., Resorable Bioceramics Based on Stabilized Calcium Phosphates. Part II: Evaluation of Biological Response, Biomaterials, vol. 22, pp. 135-150, 2001.

Bancroft et al., Fluid Flow Increases Mineralized Matrix Deposition in 3D Perfusion Culture of Marrow Stromal Osteoblasts in a Dose-dependent Manner, Proceedings of the National Academy of Sciences, vol. 99, No. 20, pp. 12600-12605, Oct. 1, 2002.

Sikavitsas et al., Biomaterials and Bone Mechanotransduction, Biomaterials, vol. 22, pp. 2581-2593, 2001.

Manney et al., Calcified Tissue International, Mechanical Stimulation Promotes Osteogenic Differentiation of Human Bone Marrow Stromal Cells on 3-D Partially Demineralized Bone Scaffolds In Vitro, vol. 74, pp. 458-468, Feb. 17, 2004.

Griffith et al., Tissue Engineering—Current Challenges and Expanding Opportunities, Science, vol. 295, pp. 1009-1014, Feb. 8, 2002.

Vaccaro, A. et al., Bone Grafting Alternatives in Spinal Surgery, The Spine Journal, vol. 2, pp. 206-213, Feb. 7, 2002.

Morigi et al., Fluid Shear Stress Modulates Surface Expression of Adhesion Molecules by Endothelial Cells, Blood, vol. 85, No. 7, pp. 1969-1703, Apr. 1, 1995.

McAllister et al., Steady and Transient fluid Shear Stress Stimulate NO Release on Osteoblasts Through Distinct Biochemical Pathways, Journal of Bone and Mineral Research, vol. 14, No. 6, pp. 930-936, Dec. 30, 1998.

Hamilton et al., Characterization of the Response of Bone Marrow-Derived Progenitor Cells to Cyclic Strain: Implications for Vascular Tissue-Engineering Applications, Tissue Engineering, vol. 10, No. 3-4, 2004, pp. 361-369.

Wick, Bioprocessing for Tissue Engineering, Research Group Highlights, School of Chemical and Biomolecular Engineering, Georgia Institute of Technology, pp. 1-9, published prior to Apr. 18, 2005.

Selected pages from the Harvard Apparatus website www.harvardapparatus.com, 2 pages, published prior to Apr. 18, 2005.

Selected pages from the Flexcell International Corporation website www.flexcellint.com, 11 pages, published prior to Apr. 18, 2005.

Selected pages from the Synthecon Incorporated website, www.synthecon.com, 1 page, published prior to Apr. 18, 2005.

Selected pages from the Wave Biotech's web site, www.wavebiotech.com, 8 pages, published prior to Apr. 18, 2005.

Selected pages from the Cole-Parmer Instrument Company's website, www.coleparmer.com, 2 pages, published prior to Apr. 18, 2004.

Selected pages from the McMaster-Carr's website, www.mcmaster.com, 4 pages, published prior to Apr. 18, 2004.

Selected pages from the For linear actuators please see www.motion-net.com, 1 page, published prior to Apr. 18, 2005.

Selected pages from the Lazar Research Laboratories, Inc. website, www.lazarlab.com, 14 pages, published prior to Apr. 18, 2004.

\* cited by examiner

CELL CULTURE METHOD AND APPARATUS FOR MECHANICALLY STIMULATING CELLS

BACKGROUND

The present invention generally relates to a cell culture method and apparatus for mechanically stimulating cells, including bone cells, ligament cells, tendon cells, cartilage cells, muscle cells, blood vessel cells, and nerve cells. Cell and tissue graft therapy have been used to treat defects for many clinical disorders, including trauma and cancer. Autografts and allografts have also been used as grafting treatments for tissue repair. However, there is a limited supply of tissue that is available for autograft transplantation. Autografting requires an additional surgery which can lead to donor site morbidity and pain. Allografts have the risks of disease transmission and transplant failure due to immune response, fracture, or non-union. Due to the limitations of grafting, alternative therapies such as tissue engineering can be used, including three-dimensional tissue engineering.

SUMMARY

Mechanical loading can enhance cell growth and engineering tissue development. For example, mechanical loading can increase bone cell proliferation and matrix production in vitro. Mechanical loading can also increase bone formation in vivo, and can help regulate bone tissue mechanical properties. Cell adaptation to mechanical loading is believed to be mediated by cell mechanotransduction, which is the process of cells detecting mechanical stimuli and converting them into biochemical signals. These signals act on effector cells (e.g., osteoclasts and osteoblasts in bone) to carry out the tissue level adaptations. Cell shear stress induced by fluid flow in the porous spaces of bone can act as a mechanical stimulus in activating mechanotransduction signaling and mediating adaptation. In vivo levels of cell shear stress are estimated to be in the range of 0.8-3 Pa. Consequently, fluid flow-induced shear stress can be used as a mechanical stimulus to study mechanotransduction in vitro. Cell mechanotransduction can be analyzed by monitoring media that has flown through a flow chamber housing cells. Additionally, cells can behave differently when cultured in a three-dimensional environment than in a two-dimensional monolayer.

In some embodiments of the present invention, a cell culture assembly is provided. The cell culture assembly can include a flow chamber positioned in a fluid path and a support comprising cells positioned within the flow chamber to expose the cells to the fluid path. The cell culture assembly can further include a means for producing a steady flow of fluid in the fluid path to transport nutrients to the cells and to carry conditioned media away from the cells, and a means for producing an oscillatory flow of fluid in the fluid path simultaneously with producing the steady flow of fluid in the fluid path to mechanically stimulate the cells.

Some embodiments of the present invention provide a cell culture assembly. The cell culture assembly can include a fluid path through which fluid flows in the cell culture assembly. The cell culture assembly can include a flow chamber positioned in the fluid path. The cell culture assembly can further include a support positioned within the flow chamber and the support may include cells. The cell culture assembly can also include a first pump and a second pump positioned in fluid communication with the flow chamber. The first pump can be adapted to produce a steady flow of fluid in the fluid path. The second pump can be adapted to produce an oscillatory flow of fluid in the fluid path simultaneously with production of the steady flow of fluid.

In some embodiments of the present invention, a method for culturing cells is provided. The method can include providing a flow chamber positioned in a fluid path. The method can further include providing a support positioned within the flow chamber, the support comprising cells. The method can also include transporting fluid in the fluid path at a substantially steady flow rate to transport fluid over the cells. The method can further include transporting fluid in the fluid path at a substantially oscillatory flow rate simultaneously with transporting fluid in the fluid path at a substantially steady flow rate.

Other features and aspects of the invention will become apparent by consideration of the detailed description, accompanying drawings and claims.

DETAILED DESCRIPTION

Figure 1:
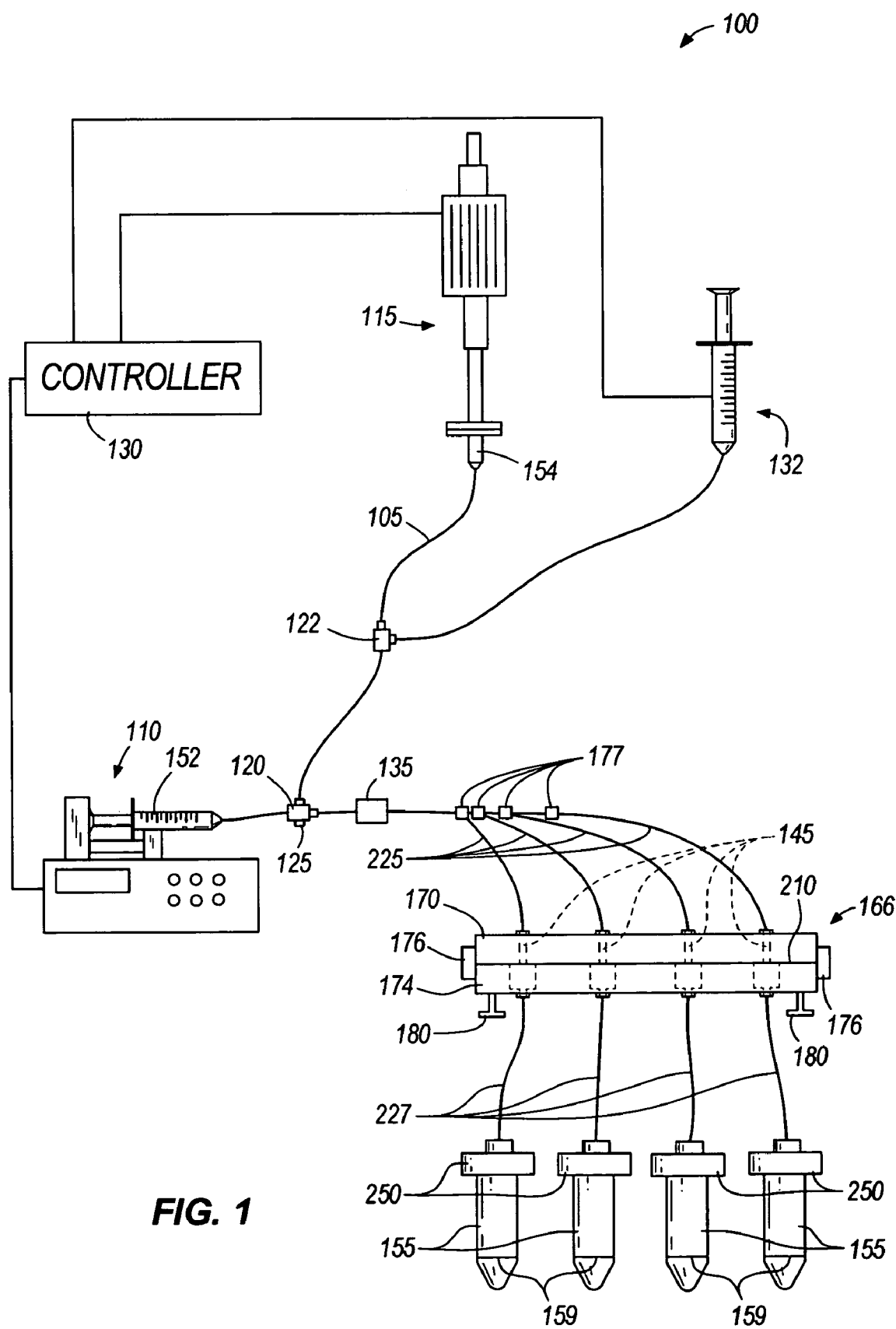
FIG. 1 is a schematic diagram of a cell culture assembly according to one embodiment of the present invention, the cell culture assembly including a plurality of flow chambers.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present invention relates to cell culture assemblies that employ a steady flow of fluid and an oscillatory flow of fluid to mechanically stimulate cells. The focus of the description below will be on a cell culture assembly for culturing bone cells on tissue engineering scaffolds. However, it should be noted that the present invention can be extended to the stimulation of other types of cells on various types of supports without departing from the spirit and scope of the present invention. That is, the present invention can be extended to the stimulation of a variety of cells, including, without limitation, bone cells, ligament cells, tendon cells, cartilage cells, muscle cells (e.g., skeletal muscle cells, cardiac muscle cells and smooth muscle cells), blood vessel cells, and nerve cells. Various aspects of the present invention have been described in a paper by J. L. Vance, S. A. Galley, and S. W. Donahue, entitled, "Mechanical stimulation of MC3T3 osteoblastic cells in a bone tissue engineering bioreactor enhances $PGE_2$ release," which was presented at the 51st Annual Meeting of the Orthopaedic Research Society in Washington DC on Feb. 21-23, 2005, and which is incorporated herein by reference.

As used herein and in the appended claims, the terms "upstream" and "downstream" refer to the direction of steady fluid movement in a cell culture assembly. That is, the term "upstream" is used to describe any location, element or process that occurs prior to the point or area being referred to relative to the direction of steady (i.e., not oscillatory) fluid movement in a cell culture assembly, whereas the term "downstream" is used to describe any location, element or process that occurs subsequent to the point or area of reference with respect to steady fluid movement in the cell culture assembly. Although oscillatory flow in the cell culture assembly may at least temporarily reverse the direction of fluid movement, the terms "upstream" and "downstream" remain defined relative to the steady flow. Furthermore, the terms "upstream" and "downstream" are defined assuming a positive steady flow in the cell culture assembly (i.e., not suction) from a first pump and a second pump to one or more flow chambers. The steady flow of fluid can include negative, reverse steady flow, but such negatively directed flow will not affect how "upstream" and "downstream" are defined herein.

As used herein and in the appended claims, the term "fluid path" refers collectively to those areas in the cell culture assembly through which fluid passes. A "fluid path" can refer to an entire path followed by fluid through the cell culture assembly or can refer to a portion of that path.

As used herein and in the appended claims, the term "flow chamber" refers to a reservoir that is positioned in a fluid path to expose at least a portion of the interior of the flow chamber to the fluid flowing in the fluid path, the flow chamber being in fluid communication with the fluid path. In some embodiments, the flow chamber serves as the final destination of the fluid path, and the fluid need not necessarily flow through the flow chamber.

As used herein and in the appended claims, the term "support" refers to any two-dimensional or three-dimensional structure to which the cells may be bound, or within which the cells can be contained. The "support" can include porous or nonporous material. The "support" can be biologically modified to enhance binding of the cells of interest, including having ligands adsorbed to the support to promote the binding of cell receptors of interest.

As used herein and in the appended claims, the term "cells" refers to a variety of cells including, but not limited to, at least one of bone cells (e.g., osteoblasts, osteoclasts, etc.), ligament cells (e.g., fibroblasts, etc.), tendon cells (e.g., fibroblasts, etc.), cartilage cells (e.g., chondrocytes, etc.), muscle cells (e.g., skeletal muscle cells, cardiac muscle cells, smooth muscle cells, etc.), blood vessel cells (e.g., smooth muscle cells, endothelial cells, etc.), and nerve cells (e.g., neurons, astrocytes, oligodendrocytes, etc.).

As used herein and in the appended claims, the term "pump" refers to a device that moves a fluid (i.e., a liquid or gas) by pressure and/or suction.

As used herein and in the appended claims, the term "steady flow" refers to a flow having a substantially steady magnitude that is substantially either all positive or all negative.

As used herein and in the appended claims, the term "oscillatory flow" refers to a flow having an oscillatory magnitude. The oscillatory flow includes a symmetrically oscillatory magnitude, an asymmetrically oscillating magnitude, and combinations thereof. In some embodiments, the oscillatory flow includes a positive portion and a negative portion. In some embodiments, the oscillatory flow includes pulsatile flow, wherein the flow is oscillatory in magnitude, but is either all positive or all negative.

As used herein and in the appended claims, the term "biomolecule" refers to a molecule, or a derivative thereof, that occurs in or is formed by a living cell. A biomolecule can include, without limitation, at least one of an amino acid, a nucleic acid, a polypeptide, a polynucleotide, a lipid, a phospholipid, a saccharide, a polysaccharide, and combinations thereof. Furthermore, a biomolecule can include, without limitation, at least one of mRNA, total RNA, genomic DNA, plasmid DNA, plant DNA, a protein, a hormone, a growth factor, an antibody, an antigen, and combinations thereof.

As used herein and in the appended claims, the term "conditioned media" refers to experimental culture media that has flown through the cell culture assembly, and which can be used for biochemical analysis. For example, the conditioned media can be collected and then analyzed for the presence of a biomolecule of interest. In some embodiments, the conditioned media can include cellular waste products.

As used herein and in the appended claims, the term "injection port" refers to a point in the fluid path wherein a biomolecule may be delivered into the fluid path. An "injection port" may be located at any point along the fluid path to allow a biomolecule to be delivered at any point along the fluid path.

Figure 2:
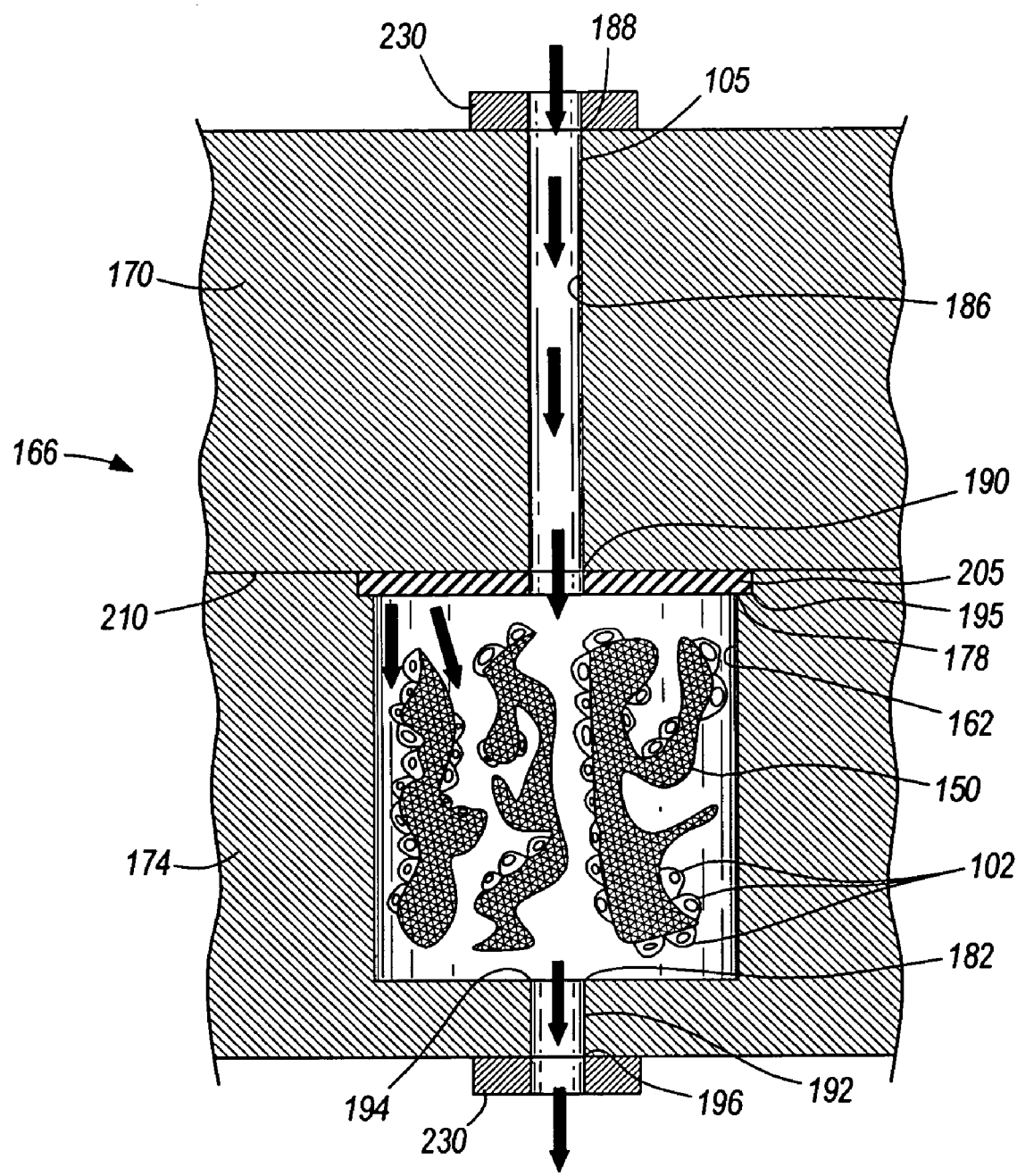
FIG. 2 is a cross-sectional view of one of the flow chambers of FIG. 1.

FIGS. 1 and 2 illustrate a cell culture assembly 100 for applying a steady flow of fluid and an oscillatory flow of fluid to cells 102 according to one embodiment of the invention. As shown in FIG. 1, the cell culture assembly 100 includes a fluid path 105 through which fluid flows in the cell culture assembly 100, a first pump 110 for producing a steady flow of fluid, and a second pump 115 for producing an oscillatory flow of fluid. The cell culture assembly 100, as shown in FIG. 1, further includes a first connector 120 (e.g., a three-way valve) positioned in the fluid path 105 to combine the steady flow and the oscillatory flow of fluid; a detector 125 for detecting at least one of the steady flow and the oscillatory flow of fluid; a controller 130 for controlling the flow rate of the steady flow of fluid, and the flow rate and frequency of the oscillatory flow of fluid; a media source 132 (e.g., a syringe) which allows for the transfer of fresh media into the fluid path 105 substantially without contamination via a second connector 122 (e.g., a three-way valve); and an injection port 135 which can be used in some embodiments to introduce a biomolecule of interest to the fluid path 105. As shown by FIGS. 1 and 2, the cell culture assembly 100 also includes one or more flow chambers 145, one or more supports 150 comprising cells 102, and one or more collection reservoirs 155. The fluid flowing through the fluid path 105 can include, but is not limited to, cell culture media. In some embodiments, transfer of fresh media into the fluid path 105 via the media source 132 is not necessary, and such embodiments do not include the media source 132.

The first pump 110 is adapted to produce a steady flow of fluid in the fluid path 105 to transport nutrients to the cells 102 and, in some embodiments, to carry conditioned media 159 away from the cells 102. The second pump 115 is adapted to produce an oscillatory flow of fluid in the fluid path 105 simultaneously with the production of the steady flow of fluid to mechanically stimulate the cells 102. The oscillatory flow of fluid generated by the second pump 115 is interposed with the steady flow of fluid generated from the first pump 110 via the first connector 120. The first connector 120 is positioned downstream from the first pump 110 and the second pump 115 and upstream from the flow chamber 145. The first connector 120 can be positioned at any position in the fluid path 105 to interpose the steady flow and oscillatory flow of fluid produced by the first pump 110 and the second pump 115, respectively. In some embodiments, the first pump 110 and the second pump 115 are each directly fluidly coupled to each flow chamber 145, or to a manifold that supplies fluid to each flow chamber 145, and such embodiments do not include the first connector 120.

Each flow chamber 145 is positioned downstream from and is fluidly coupled to the first connector 120. Each flow chamber 145 includes a support 150. The flow chamber 145 and the support 150 are positioned to expose at least a portion of the flow chamber 145 and the support 150 to fluid flowing in the fluid path 105. Each collection reservoir 155 is positioned downstream from and is fluidly coupled to a flow chamber 145 to collect conditioned media 159 from the flow chamber 145.

The detector 125 is positioned downstream from one or both of the first pump 110 and the second pump 115, and can be fluidly coupled to the fluid path 105 at any point along the fluid path 105. In some embodiments, the detector 125 includes a flow probe (e.g., In-line Series Flowprobes flow probe, available from Transonic Systems Inc.®, Ithaca, N.Y.) for measuring the flow rate and/or frequency of the fluid flowing in the fluid path 105. The detector 125 can be used to monitor one or more of the following from at least one of the first pump 110 and the second pump 115: flow rate, pressure, temperature, frequency, etc.

In some embodiments, the detector 125 is adapted to send feedback to the controller 130, which can control at least one of the first pump 110 and the second pump 115, based upon the feedback from the detector 125. The media source 132 can be manually activated to deliver fresh media to the fluid path 105, or the media source 132 can include a programmable pump, or a pump that can be controlled by the controller 130, similar to that of the first pump 110 and the second pump 115. Similarly, the injection port 135 can include a manually-driven device to introduce a biomolecule of interest to the fluid path 105, or the injection port 135 can include an electronically-driven or programmable pump that can be controlled by the controller 130.

The controller 130 can be connected to the first pump 110, the second pump 115, the detector 125, and in some embodiments, the media source 132. In some embodiments, the controller 130 of the cell culture assembly 100 is microprocessor-based and is adapted to manipulate and control the first pump 110 to control the flow rate of the steady flow of fluid, and/or the second pump 115 to control the flow rate and frequency of the oscillatory flow of fluid. Additionally, in some embodiments, the controller 130 can control the flow rate at which fresh media is introduced to the fluid path 105 via the media source 132. In other embodiments, the controller 130 can include any programmable or non-programmable electronic system, and need not necessarily be microprocessor-based. The controller 130 can include any combination of hardware and/or software components, and can include more than one controller device. In addition, the controller 130 can include one or more independently-functioning or dependently-functioning units, such as a first controller that controls the first pump 110, a second controller that controls the second pump 115, and a third controller that controls the media source 132. By way of example only, the controller 130 can include any number of discrete logic elements coupled together to perform the same function(s) as described above. Still other types of electronic controllers capable of performing these function are possible, would be readily recognized by those skilled in the art, and fall within the spirit and scope of the present invention. In some embodiments, the first pump 110, the second pump 110, the media source 132, and/or a driving device for delivering fluid via the injection port 135 can be controlled manually, and the controller 130 is not required.

The injection port 135 of the illustrated embodiment is positioned downstream in the fluid path 105 from the first pump 110 and the second pump 115, and upstream from the flow chamber 145. However, the injection port 135 can be positioned at any point in the fluid path 105 upstream of the flow chambers 145 to introduce a biomolecule of interest to the fluid path 105 to produce a desired effect in the cells 102. For example, in some embodiments, the cells 102 include bone cells, and a parathyroid hormone can be delivered (e.g., as a bolus injection) at the injection port 135 prior to (e.g., about 30 minutes before) activating the second pump 115 and introducing the mechanically-stimulating oscillatory flow of fluid to the cells 102. Parathyroid hormone has been found to increase the responsiveness of bone cells to mechanical stimulation. Other biomolecules of interest can be delivered in a similar manner, depending on the cells 102 used, and the desired effect. In some embodiments, a plurality of injection ports 135 can be used to introduce a variety of biomolecules to the fluid path 105. In other embodiments, introduction of a biomolecule to the fluid path 105 is not necessary, and the cell culture assembly 100 does not include an injection port 135.

The first pump 110 can include, but is not limited to, at least one of a syringe pump, a peristaltic pump, and some other type of linear or non-linear actuator. For example, in some embodiments, such as the embodiment illustrated in FIG. 1, the first pump 110 includes a programmable syringe pump (e.g., a Remote Infuse/Withdraw PHD 4400 Hpsi Programmable Syringe Pump, available from Harvard Apparatus, Holliston, Mass.) coupled to a first fluid source 152 (e.g., a syringe) where the first pump 110 forces the first fluid source 152 to drive fluid through the fluid path 105. In some embodiments, the first pump 110 includes an electro-magnetically driven linear actuator (e.g., LINEAR MOTORS LINMOT® P linear motor, available from LinMot® Inc., Delavan, Wis.) coupled to the first fluid source 152.

The second pump 115 can include, but is not limited to, at least one of a syringe pump and some other type of linear or non-linear actuator. For example, in some embodiments, such as the embodiment illustrated in FIG. 1, the second pump 115 includes an electro-magnetically driven linear actuator (e.g., LINEAR MOTORS LINMOT® P linear motor, available from LinMot® Inc., Delavan, Wis.) coupled to a second fluid source 154 (e.g., a syringe), such that the first pump 115 forces the second fluid source 152 to drive fluid through the fluid path 105. It should be understood that the first and second fluid sources 152, 154 do not need to include syringes, but rather can include a variety of types of fluid sources known to those of ordinary skill in the art.

In some embodiments, the one or more flow chambers 145 are defined at least partially by an inner surface 162 of a body 166. As shown in FIG. 1, the body 166 includes a first portion 170 and a second portion 174, which can move relative to one another to allow a support 150 to be placed inside each flow chamber 145. The first portion 170 and the second portion 174 can be sealed together and held in a sealed positioned by one or more closures 176. As shown in FIG. 1, the body 166 includes two legs 180 coupled to the second portion 174 of the body 166. The legs 180 can be used to hold the second portion 174 in place while a support 150 is positioned within, or removed from, each flow chamber 145. The closures 176 and legs 180 are illustrated by way of example only, but it should be understood by one of ordinary skill in the art that the body 166 can be sealed and supported in a variety of other ways without departing from the spirit and scope of the present invention. Furthermore, the body 166 illustrated in FIGS. 1 and 2 is shown by way of example only. In some embodiments, the body 166 only includes one portion that defines the flow chambers 145. Other bodies 166 and flow chamber structures and shapes can be used without departing from the spirit and scope of the present invention.

In the embodiment illustrated in FIG. 1, the flow chambers 145 are fluidly coupled in parallel to the first pump 110 and the second pump 115 via the first connector 120. In some embodiments, as shown in FIG. 1, each flow chamber 145 is connected to the fluid path 105 downstream of the first connector 120 via a third connector 177 (e.g., a three-way valve). In some embodiments employing more than one flow chamber 145, the flow chambers 145 are fluidly coupled in series to the first pump 110 and the second pump 115, such that conditioned media 159 flows from one flow chamber 145 into another flow chamber 145, and a collection reservoir 155, if employed, is fluidly coupled to the last flow chamber 145. In the embodiment illustrated in FIG. 1, the body 166 includes four flow chambers 145. However, it should be understood that the body 166 can include as few as one flow chamber 145 and as many as structurally feasible or necessary for a particular application. For the sake of clarity and brevity, one flow chamber 145 will be described herein.

The body 166 can be formed of a variety of materials including, but not limited to, a polymer, such as acrylic or polycarbonate, and combinations thereof. Accordingly, the flow chamber 145 can be formed in the body 166 by a variety of methods, including, without limitation, at least one of molding, casting, forging and machining. As illustrated in FIG. 2, the flow chamber 145 includes an inlet 178 positioned to allow fluid to enter the flow chamber 145 and an outlet 182 positioned to allow fluid to exit the flow chamber 145. However, in some embodiments, the flow chamber 145 may not include an outlet 182 and the flow chamber 145 may serve as the final destination in the fluid path 105.

The first portion 170 of the body 166 includes a first bore 186 defined therein that includes a first opening 188, which is in fluid communication with the first connector 120, and a second opening 190, which is in fluid communication with the inlet 178 of the flow chamber 145. The second portion 174 includes a second bore 192 defined therein that includes a first opening 194, which is fluid communication with the outlet 182 of the flow chamber 145, and a second opening 196, which is in fluid communication with the collection reservoir 155. Thus, the first opening 188 of the first bore 186 defines an inlet in the body 166, and the second opening 196 of the second bore 192 defines an outlet in the body 166.

The first bore 186 and the second bore 192 can have a variety of dimensions. In some embodiments, the first bore 186 and the second bore 192 are substantially cylindrical and each have a diameter. In the embodiment illustrated in FIG. 2, the inlet 178 of the flow chamber 145 has a diameter greater than that of the first bore 186 and the outlet 182 of the flow chamber 145 to allow for the support 150 to be positioned and maintained within the flow chamber 145. For example, in some embodiments, the diameter of the first bore 186 and the diameter of the outlet 182 of the flow chamber 145 are each about 0.125 inches, and the diameter of the inlet 178 of the flow chamber 145 is about 1 inch to allow the support 150 to be positioned within the flow chamber 145.

A recess 195 is further defined in the second portion 174 of the body 166 adjacent the inlet 178 of the flow chamber 145.

As shown in FIG. 2, the recess 195 is also substantially cylindrical in shape and has a diameter greater than the diameter of the inlet 178 of the flow chamber 145. A seal-forming device 205 (e.g., an o-ring, such as a #11 VITON® o-ring, available from Allorings.com, Inc., Hampton Falls, N.H.) is positioned within the recess 195 to fluidly seal the first portion 170 and the second portion 174 of the body 166 along an interface 210. The seal-forming device 205 includes an aperture with a diameter about equal to that of the first bore 186 to allow fluid to pass through the seal-forming device 205 and into the flow chamber 145.

In some embodiments, the first opening 188 of the first bore 186 is fluidly coupled to the first connector 120 via a first tubing 225 and the second opening 196 of the second bore 192 is fluidly coupled to the collection reservoir 155 via a second tubing 227. In some embodiments, the first tubing 225 is fluidly coupled to the first opening 188 of the first bore 186, and the second tubing 227 is fluidly coupled to the outlet 182 of the flow chamber 145 via barbed male-male connectors, as are well-known to those of ordinary skill in the art. Seal-forming devices 230 (e.g., o-rings) can be used to fluidly seal the first tubing 225 and the second tubing 227 to the body 166. In some embodiments, the first tubing 225 and the second tubing 227 include silicone tubing that is permeable to oxygen and carbon dioxide to ensure gas exchange between the cells 102 in the flow chamber 145 and the environment (e.g., silicon tubing, available from Harvard Apparatus, Holliston, Mass.).

In the embodiment illustrated in FIG. 2, the support 150 is positioned within the flow chamber 145. In some embodiments, the support 150 can include, but is not limited to, at least one of a scaffold, a matrix, a gel, and combinations thereof. For example, in some embodiments, the support 150 includes a substantially cylindrical, porous calcium phosphate scaffold (e.g., a 3D Calcium Phosphate Scaffold, available from BD™ Biosciences, Bedford, Mass,).

Cells 102 can be positioned within the flow chamber 145 in a variety of ways. In some embodiments, the cells 102 are seeded onto the support 150, and then the seeded support 150 is positioned within the flow chamber 145. In some embodiments, the cells 102 are suspended within the support 150 (e.g., within a porous support 150), and then the support 150 containing the cells 102 is positioned within the flow chamber 145. In some embodiments, the cells 102 are suspended within the flow chamber 145, and the inlet 178 and the outlet 182 are each fitted with a filter to prevent the cells 102 from flowing out of the flow chamber 145. In some embodiments, the cells are seeded directly onto the inner surface 162 of the body 166, such that the inner surface 162 of the body 166 functions as a two-dimensional support positioned within the flow chamber 145.

The cells 102 can include, but are not limited to, bone cells. In some embodiments, the cells 102 include osteoblasts and osteoclasts, and combinations thereof. For example, the cells 102 can include a mouse osteoblastic cell line (e.g., MC3T3 subclone 4 mouse osteoblastic cell line, available from ATCC, The Global Biosource Center™, Manassas, Va.).

In some embodiments, as shown in FIG. 1, the cell culture assembly 100 includes four collection reservoirs 155. However, it should be understood that as few as one collection reservoir 155 and as many as structurally feasible, or necessary for a particular application, are possible. The collection reservoir 155 can be formed by a variety of methods. In some embodiments, as shown in FIG. 1, the collection reservoir 155 includes a centrifuge tube having a bore defined in its cap 250 that is sealed by a seal-forming device (e.g., an o-ring), which allows for facile removal and replacement of the collection reservoir 155.

In operation, regardless of how the cells 102 are positioned within the flow chamber 145, fluid is supplied to the first pump 110 and the second pump 115, and the first pump 110 produces a steady flow of fluid and the second pump 115 produces an oscillatory flow of fluid simultaneously with the steady flow of fluid through the fluid path 105. The fluids flowing from the first pump 110 and the second pump 115 are combined at the first connector 120, and the combined steady flow and oscillatory flow of fluid flows the inlet 178 of flow chamber 145 (via the first opening 188 of the first bore 186 in the first portion 170 of the body 166). The fluid flows through the flow chamber 145 and, as the fluid flows through the flow chamber 145, the cells 102 seeded on the support 150 are subjected to both a steady perfusion of fluid, which transports nutrients to the cells 102 and carries conditioned media 159 away from the cells 102, and an oscillatory flow of fluid simultaneously with the steady flow of fluid, which mechanically stimulates the cells 102. The fluid may continue to move through the fluid path 105 and exit the flow chamber 145 through the outlet 182. The fluid can be altered by the cells 102, becoming conditioned media 159, which can be collected by the collection reservoir 155.

The first pump 110 and the second pump 115 are capable of producing a variety of volumetric flow rates, and in addition, the second pump 115 is capable of producing a variety of flow rates having a variety of frequencies. For example, in some embodiments, the second pump 115 produces a volumetric flow rate of about 40 mL/min., with a frequency of about 2 Hz. In some embodiments, the frequency of the flow produced by the second pump 115 is within a generally physiological frequency range (e.g., from about 0.1 Hz to about 10 Hz). In some embodiments, the first pump 110 is produces a volumetric flow rate of about 0.025 mL/min. In some embodiments, the first pump 110 is adapted to produce a constant low flow rate perfusion, relative to that produced by the second pump 115.

In some embodiments, the second pump 115 is adapted to produce a constant oscillatory flow of fluid in the fluid path 105. In some embodiments, the second pump 115 is adapted to produce an intermittent oscillatory flow of fluid. For example, in some embodiments, the second pump 115 produces an oscillatory flow of fluid at least once daily for a period of no greater than about 30 minutes.

Cells 102 that may benefit from exposure to a constant steady flow of fluid from the first pump 110 combined with a constant oscillatory flow of fluid from the second pump 115 include, but are not limited to, cardiac muscle cells and blood vessel cells. Cells 102 that may benefit from exposure to a constant steady flow of fluid from the first pump 110 and an intermittent oscillatory flow of fluid from the second pump 115 include, but are not limited to, bone cells, ligament cells, tendon cells, and cartilage cells.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described herein are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

The following working examples are intended to be illustrative and not limiting.

EXAMPLE 1

This example describes one embodiment of a cell culture assembly 100 of the present invention. Four flow chambers 145 were machined out of a polycarbonate body 166, and each flow chamber 145 housed the cell-seeded supports 150 during experimentation. The polycarbonate body 166 included a first portion 170 and a second portion 174, and the flow chambers 145 were machined out of the second portion 174. Four first bores 186 were machined out of the first portion 170, and each first bore 186 was positioned in fluid communication with the an inlet 178 of each flow chamber 145. Four second bores 192 were machined out of the second portion 174, and each second bore 192 was coupled to an outlet 182 of the flow chamber 145. Each flow chamber 145 had a single 1-inch inlet 178 and a single ⅛-inch outlet 182. An ⅛-inch barbed connector was threaded into an opening 188 of each first bore 186, and connected to an ⅛-inch silicon tubing. The body 166 included two steel legs 180 that were screwed into a bottom surface of the second portion 174 of the polycarbonate body 166. The two steel legs 180 served to support the body 166 when the supports 150 were being placed into their respective flow chambers 145. Each flow chamber 145 was fluidly coupled to a first pump 110, specifically a syringe pump (available from Harvard Apparatus, Hollistion, Mass.) coupled to a first fluid source 152 for producing a steady flow of fluid, and a second pump 115, specifically an electromagnetic linear actuator (available from Linmot, Delavan, Wis.) coupled to a second fluid source 154 for producing an oscillatory flow of fluid. Each chamber 145 was also fluidly coupled to a media source 132, and specifically, to a 140 mL syringe. Each flow chamber 145 was also fluidly coupled to a collection reservoir 155. The collection reservoirs 155 used to collect conditioned media 159 from the cells 102 included 50 mL centrifuge tubes with an ⅛-inch hole drilled in the cap 250, and an ⅛-inch male-male tubing barb with an #8 VITON® o-ring (available from Allorings.com, Inc., Hampton Falls, N.H.) sealing the tubing to the cap 250. The first pump 110 provided the constant low flow rate perfusion, and the second pump 115 generated a larger magnitude with an oscillatory flow profile. Thus, the cell culture assembly 100 provided perfusion with mechanical stimulation. Flow rates and profiles were monitored with a detector 125. The detector 125 included a flow probe (available from Transonic Systems Inc., Ithaca, N.Y.). A first connector 120, specifically a three-way valve, was used to combine the fluid flowing from the first pump 110 and the fluid flowing from the second pump 115. A second connector 122, specifically a three-way valve, allowed for the transfer of fresh media from the media source 132 into the system without risk of contamination. Each flow chamber 145 was coupled to the first connector 120 via a third connector 117, specifically, a three-way valve. The body 166 was kept in an incubator at 37° C., 5% carbon dioxide during experimentation.

EXAMPLE 2

This example describes a method that was used to culture cells 102 using the cell culture assembly set forth in Example 1, compared with cells cultured in static conditions, and cells cultured with perfusion flow alone. The supports 150 used included a 3D cylindrical, porous calcium phosphate scaffold with a 5 mm diameter and a 3.5 mm height. The cells 102 used for mechanical stimulation included a mouse osteoblastic cell line MC3T3 subclone 4. The cells 102 were first cultured in standard MC3T3 media comprising MEM-α (e.g., GIBCO® Advanced MEM basal media, available from Invitrogen™, Carlsbad, Calif.), 10% fetal bovine serum (e.g., BOVINE GROWTH SERUM™ fetal bovine serum, available from HyClone, Logan, Utah), and 1% penicillin/streptomycin (CELLGRO® penicillin/streptomycin, available from Mediatech, Inc., Herndon, Va.). The cells 102 were then statically seeded on the supports 150 by suspending 100,000 cells 102 in 40 μl of media and then seeding the resulting suspension onto the supports 150. The seeded supports 150 were then incubated at 37° C. for 1 hour in a 24-well plate to allow the cells 102 to adhere to the supports 150. The cell-seeded supports 150 were covered with 2 mL of media and allowed to incubate for 24 hours prior to being loaded into the flow chambers 145. Following the incubation period, the supports 150 were positioned in the flow chambers 145, which were kept in an incubator at 37° C., 5% carbon dioxide. MC3T3 media perfusion was initiated by the first pump 110 at a rate of 0.025 ml/min. Four hours after perfusion began, the first mechanical loading bout (i.e., an oscillatory fluid flow) was initiated by the second pump 115 at a rate of 40 mL/min, with a frequency of 1 Hz for 30 min, to allow exposure of the cells 102 to an intermittent oscillatory flow superimposed with the steady perfusion from the first pump 110. One bout of oscillatory fluid flow was performed daily for 2 days. For static culture conditions, the supports 150 remained in 24-well plates with 2 mL of MC3T3 media. For the static cultures, media changes were performed every 24 hours. The incubator was maintained at 37° C., with 5% $CO_2$ throughout the duration of the experiment. DNA and prostaglandin $E_2$ were quantified for six supports 150 for each condition (static, perfusion, and perfusion with mechanical stimulation) at both 24 and 48 hours for a total of 36 supports 150.

The steady flow of fluid was estimated to expose the cells 102 to a shear stress of about 0.0008 Pa, and the oscillatory flow of fluid was estimated to expose the cells 102 to a shear stress of 1.3 Pa once daily for a period of 30 min. at 1 Hz for the perfusion with mechanical stimulation group. Every 24 hours, conditioned media 159 was collected and analyzed for prostaglandin E2 ($PGE_2$) using a BIOTRAK™ PGE2 competitive enzyme immunoassay (available from Amersham Biosciences, Piscataway, N.J.).

The supports 150 were removed after 24 or 48 hours and genomic DNA was isolated using the GenomicPrep kit (available from Amersham Biosciences, Piscataway, N.J.). Cell membranes were lysed while the DNA remained hydrated, RNA was degraded using RNase A, and protein was precipitated and discarded. DNA was isolated using isopropanol precipitation and washed with 70% ethanol. After isolation, total DNA was quantified with a Nanodrop Spectrophotometer (available from Nanodrop Technologies, Rockland, Del.).

Every 24 hours, conditioned media 159 was collected from the flow chambers 145, and the 24-well plates that contained the statically cultured supports 150. The conditioned media was frozen at −20° C. The $PGE_2$ levels were determined using a BIOTRAK™ $PGE_2$ competitive enzyme immunoassay (available from Amersham Biosciences, Piscataway, N.J.). The assay was performed in duplicate using 50 μL samples from all conditioned media 159 samples. The reaction was halted prior to endpoint determination using 1M sulfuric acid and read at 450 nm using a VERSAmax microplate reader (available from Molecular Devices Corporation, Sunnyvale, Calif.). The duplicate optical density values were corrected for nonspecific binding and averaged, and compared to a standard curve to determine the amount of $PGE_2$ in each sample. These values were normalized by the total genomic DNA in the corresponding support 150. Analysis of variance for normalized $PGE_2$ levels were followed up by Fisher's PLSD test at a significance level of 0.05 using SAS statistical software.

Figure 3:
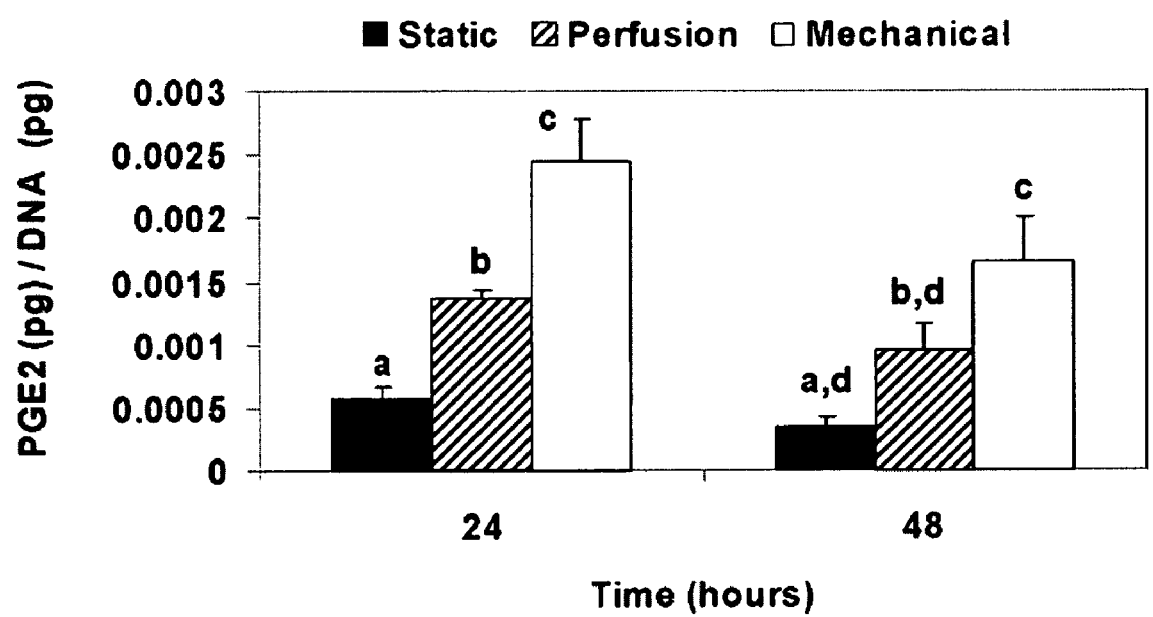
FIG. 3 is a bar graph illustrating experimental results for culturing bone cells in a cell culture assembly according to one embodiment of the present invention, as described in Examples 1 and 2.

As shown in FIG. 3, at 24 hours, both perfusion flow alone and perfusion flow with mechanical stimulation significantly ($p<0.001$) increased $PGE_2$ release from the cells 102 seeded on the supports 150, compared to static controls. The greatest increase was in the mechanical stimulation group, which had $PGE_2$ levels significantly larger than the other two groups. Perfusion flow caused a 2.5-fold increase in $PGE_2$ levels compared to static culture after 24 hours, and mechanical loading caused a 4.5-fold increase. Similar trends were seen at 48 hours; however the difference between the static and perfusion groups was not significant. With continued reference to FIG. 3, at 48 hours, the mechanical group was significantly ($p<0.034$) different from the perfusion and static groups. Mechanical stimulation produced about 80% more $PGE_2$ release than perfusion flow after 24 hours, and 77% more after 48 hours.

What is claimed is:

1. A method for culturing cells, the method comprising:
providing a flow chamber positioned in a fluid path;
providing a porous support positioned within the flow chamber, the support comprising cells;
transporting fluid in the fluid path at a substantially steady flow rate to transport fluid past the cells; and
transporting fluid in the fluid path at a substantially oscillatory flow rate simultaneously with transporting fluid in the fluid path at a substantially steady flow rate, wherein the oscillatory transport of fluid occurs intermittently.

2. The method of claim 1, further comprising detecting at least one of the substantially steady flow rate and the substantially oscillatory flow rate in the fluid path.

3. The method of claim 2, further comprising controlling at least one of the substantially steady flow rate and the substantially oscillatory flow rate responsive to detecting at least one of the substantially steady flow rate and the substantially oscillatory flow rate in the fluid path.

4. The method of claim 1, further comprising delivering a biomolecule to the fluid path, the biomolecule adapted to produce a desired effect in the cells.

5. The method of claim 1, wherein transporting fluid in the fluid path at a substantially steady flow rate includes transporting nutrients to the cells and transporting conditioned media away from the cells.

6. The method of claim 1, wherein transporting fluid in the fluid path at a substantially oscillatory flow rate includes mechanically stimulating the cells.

7. The method of claim 1, wherein transporting fluid in the fluid path at a substantially steady flow rate includes transporting fluid at a volumetric flow rate ranging from about 0.01 mL/min to about 3 mL/mm.

8. The method of claim 1, wherein the intermittent oscillatory fluid transport occurs thirty minutes per day.

* * * * *